United States Patent [19]

Steckelberg et al.

[11] 4,118,324

[45] Oct. 3, 1978

[54] FABRIC SOFTENERS

[75] Inventors: Willi Steckelberg, Hofheim am Taunus; Hans Ludwig Panke, Frankfurt am Main; Adolf May, Hofheim am Taunus; Hans-Walter Bücking, Kelkheim, all of Fed. Rep. of Germany

[73] Assignee: Hoechst Aktiengesellschaft, Frankfurt am Main, Fed. Rep. of Germany

[21] Appl. No.: 807,402

[22] Filed: Jun. 17, 1977

[30] Foreign Application Priority Data

Nov. 13, 1976 [DE] Fed. Rep. of Germany ....... 2651898

[51] Int. Cl.² .......................................... D06M 13/46
[52] U.S. Cl. .................................... 252/8.9; 252/8.75; 252/8.8
[58] Field of Search ..................... 252/8.9, 8.8, 8.75

[56] References Cited

U.S. PATENT DOCUMENTS

| 3,356,526 | 12/1967 | Waldman et al. | 252/8.8 |
| 3,636,114 | 1/1972 | Tobler et al. | 252/8.75 |
| 3,703,480 | 11/1972 | Grand et al. | 252/8.75 |
| 4,038,196 | 7/1977 | Minegishi et al. | 252/8.8 |

*Primary Examiner*—William E. Schulz
*Attorney, Agent, or Firm*—Connolly and Hutz

[57] ABSTRACT

Fabric softeners in the form of aqueous solutions or dispersions which contain as active ingredient one or several compounds of the formula I

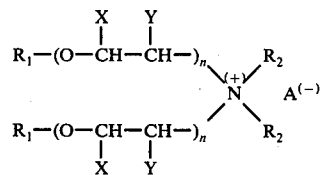

wherein $R_1$ is long-chain alkyl, X and Y are hydrogen or methyl, X and Y not being methyl simultaneously, $n$ is an integer of 1 to 20, $R_2$ is lower alkyl and A is an anion.

3 Claims, No Drawings

FABRIC SOFTENERS

The present invention relates to fabric softeners.

It is known that washed textile materials, especially those made of cellulose fibers, show an unpleasant hard feel after drying. This is particularly the case, if the washing was performed in a washing machine. This undesired hard feel can be avoided by treating the textile materials after washing in a rinsing bath with cationic substances which contain at least two longchain aliphatic radicals in the molecule. In practice, especially the dialkyldimethylammonium salts which can be suspended in water have proved to be suitable for this purpose. These products have the drawback, however, that they contain in their preferred commercial forms as concentrated solutions an inflammable alcohol. Thus, the product falls within the guide lines for dangerous working materials, due to the low flash point for transport, storage and processing. It has therefore been an objective to prepare fabric softeners which are free from solvents.

It has now been found that fabric softeners can be prepared in the form of aqueous solutions or dispersions, if as active ingredient there are used compounds of the formula I

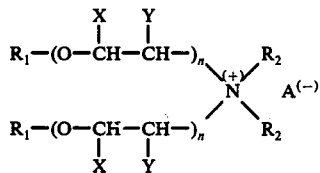

or mixtures thereof, in which $R_1$ represents identical or different aliphatic radicals having 8 to 30 carbon atoms, preferably 14 to 24 carbon atoms, cyclohexyl groups or aryl groups optionally substituted by alkyl groups, X and Y stand for a hydrogen atom or a methyl group, however, X and Y not being methyl at the same time, $n$ is an integer of 1 to 20, preferably of 1 to 5, $R_2$ represents benzyl groups or identical or different alkyl groups having 1 to 4 carbon atoms, preferably methyl groups, and A is a methosulfate, methophosphate, bromide, or preferably a chloride ion.

The quaternary etheramines of the formula I are obtained in accordance with the process described in German Patent Application No. P 26 28 157.2 by reacting secondary etheramines of the formula II

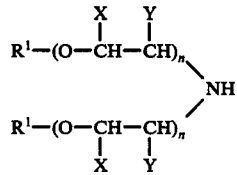

with alkylating agents of the formula III $$R^2 - A \qquad \text{III,}$$

for example, alkyl halides, alkyl-sulfuric acid esters or benzyl chloride in the presence of alkali.

The secondary etheramines of the formula (II) are obtained according to the process described in German Patent Application No. P 25 55 895.6-42 by reacting oxalkylates of the formula IV

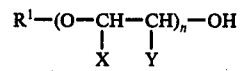

in the liquid phase with ammonia and hydrogen in the presence of hydrogenation-dehydrogenation catalysts, especially nickel and cobalt catalysts, with a gas rate of at least 10 l/kg of oxalkylate . h at a temperature of from 150° to 250° C. and in the range of atmospheric pressure at 0.5 to 1.5 atmospheres gage, and by eliminating the reaction water with the gas stream. The symbols $R^1$, $R^2$, X, Y, $n$ and A in the formulae II, III and IV are defined as in formula I above.

The saturated and unsaturated alcohols which are at the basis of the oxyalkyl derivatives of the formula IV and which form the radical $R^1$ in the compounds of the formula I may be those compounds which contain a primary, secondary or tertiary alcoholic group in the molecule. The alkyl radical may be straightchained or branched and is derived from a corresponding alcohol, for example, octyl alcohol, isononyl alcohol, lauryl alcohol, isotridecyl alcohol, oleyl alcohol, stearyl alcohol; moreover, there may be mentioned mixtures of these alcohols, especially those which are formed in the hydrogenation of natural fatty acids and/or their esters, for example, tallow fat alcohols, palm oil alcohols and coconut oil alcohols. Further alcohols of which the radical $R^1$ may be derived are those which are obtained in technical processes, for example, according to the Ziegler process (ethylene synthesis process) which yields saturated primary alcohols having a straight carbon chain of up to about 24 carbon atoms, and according to the various oxo processes which produce more or less branched alcohols. Besides, there may be mentioned aromatic hydroxy compounds, such as phenol, naphthols, 2,4,6-tritertiary butyl-phenol, 4-i-nonyl-phenol, 4-i-octylphenol, 4-i-propylphenol, cresol, xylene- and 4-i-dodecylphenol.

The oxalkylene group

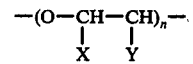

is derived preferably from ethylene or propylene oxide and is introduced by the reaction of the above-mentioned alcohols and aromatic hydroxy compounds with ethylene- and/or propylene oxide. In this process there may also be used mixtures of ethylene oxide and propylene oxide, or the reaction may be effected first with ethylene oxide and then with propylene oxide.

The reaction of the secondary etheramines of the formula II with the alkylating agents of the formula III is effected according to the methods generally known in chemistry for the preparation of quaternized ammonium compounds. As alkali there may be mentioned above all sodium hydroxide. The reaction is carried out either in water or in organic solvents. In the latter case, the solvent is to be distilled off after the reaction has been completed. The remaining reaction product is then made up to the desired final concentration with water. If the quaternization reaction is effected in water, the aqueous solution or dispersion obtained may be used directly. For the treatment of the textile material, there is generally sufficient a bath which contains from 1 to 15% by weight, preferably from 4 to 10% by weight, of one or several compounds of the formula I. These fabric softeners may be sold in commerce in the form of concentrates which contain from 20 to 35% by weight of the compound of the formula I. These concentrates are then diluted with water to the appropriate concentration needed for application as indicated above.

Furthermore, the fabric softeners of the present invention may also contain further substances and auxiliaries which are either admixed already to the concentrate of the quaternary ammonium compound of the formula I or are added separately to the aqueous solutions or dispersions or to the treating baths meant for use. These are substances or auxiliaries which have already been used in softening compositions; they include, for example, cationic or non-ionogenic surface-active substances, electrolytes, neutralizing agents, organic complexing agents, optical brighteners or solubilizers, as well as dyestuffs and perfumes.

Additives of this kind serve, for example, to further influence the feel of the fabric or other properties of the textile goods to be treated, or the adjustment of the viscosity, the pH adjustment, or further promote the stability of the solutions at low temperatures.

These fabric softener compositions are generally used by introducing the solution or dispersion containing the active ingredient into the last rinsing bath of the washing process. They impart a pleasant and soft feel to any textile material, especially those made of natural or regenerated cellulose, wool, cellulose acetate, triacetate, polyamide, polyacrylonitrile, polyester and polypropylene. Their use is particularly advantageous as fabric softeners for terry fabrics and underwear.

The preparation of the quaternary ammonium compounds of formula I is further illustrated in the following Examples. Unless otherwise stated, all quantitative data are released to the weight.

EXAMPLE 1

400 Parts of a secondary etheramine, molecular weight 787, with 1.78% of nitrogen showing an alkaline reaction, said etheramine having been obtained by the aminolysis of a straight-chain $C_{20/22}$-alcohol with 2 moles of ethylene oxide, are heated with 30.3 parts of sodium hydroxide and 40 parts of water in a laboratory autoclave having a capacity of 2 liters at a temperature in the range of from 70° to 80° C., in which process methyl chloride is pressed on the mixture up to a pressure of 5 kp/cm². When no methyl chloride is absorbed any more by the reaction mixture, the latter is aired and the product is filled off, which has the following formula

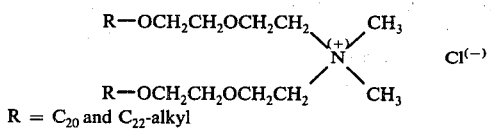

R = $C_{20}$ and $C_{22}$-alkyl

The degree of quaternization is 98%, 2% being free amine and ammonium chloride. The product can be emulsified in water. Its 1% aqueous solution shows a pH value of from 4 to 5.

EXAMPLE 2

The solution of 100 parts of a secondary etheramine, molecular weight of 615 with 2.7% of nitrogen showing an alkaline reaction, said etheramine having been obtained by the aminolysis of a stearyl alcohol reacted with 1 mole of ethylene oxide, is introduced into 100 parts of toluene in a reaction flask provided with a dropping funnel, stirrer and thermometer; after having added 40 parts of sodium carbonate, 20.5 parts of dimethyl sulfate are added dropwise, while stirring, at 60° C. within 15 minutes. After having stirred the mixture for 2 hours at 60° C., it is filtered, and 20.5 parts of dimethyl sulfate are added dropwise once more to the filtrate at 60° C. within 15 minutes. Upon stirring the mixture again for 2 hours at 60° C., the toluene is distilled off, and a product corresponding to the formula

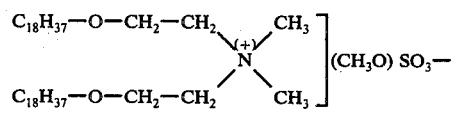

is obtained in a yield of 99%.

In an analogous manner, the following compounds are obtained:

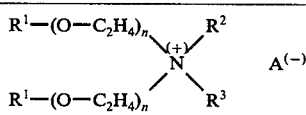

| $R^1$ | n | $R^2$ | $R^3$ | $A^{(-)}$ | Content of nitrogen showing an alkaline reaction in the starting compound |
|---|---|---|---|---|---|
| $(C_4H_9)_3$—$C_6H_2$ | 2 | $CH_3$ | $CH_3$ | $(CH_3O)SO_3$ | 1.79 |
| cyclohexyl | 6 | $C_2H_4$ | $CH_3$ | $(C_2H_4O)SO_3$ | 1.72 |
| $C_{12/14}$(33% of $C_{12}$, 64% of $C_{14}$) | 3 | $CH_3$ | $CH_3$ | Cl | 2.15 |
| isotridecyl | 3 | $CH_3$ | $CH_2C_6H_5$ | $(CH_3O)SO_3$ | 2.13 |
| coconut oil alkyl | 2 | $CH_3$ | $CH_3$ | Cl | 2.38 |
| tallow fat alkyl | 5 | $CH_3$ | $CH_3$ | Cl | 2.25 |
| oleyl | 2 | $CH_3$ | $CH_3$ | Cl | 2.01 |

We claim:
1. Fabric softeners in the form of aqueous solutions or dispersions, which contain an active ingredient one or several compounds of the formula

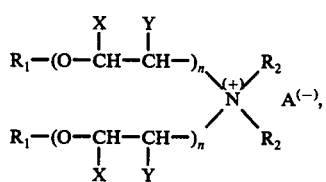

in which $R_1$ represents identical or different aliphatic radicals having 8 to 30 carbon atoms, cyclohexyl groups or aryl groups optionally substituted by alkyl groups, X and Y stand for a hydrogen atom or a methyl group, however, X and Y not being methyl at the same time, $n$ is an integer of 1 to 20, $R_2$ represents alkyl groups having 1 to 4 carbon atoms or benzyl groups, and A is a methosulfate, chloride, bromide or methophosphate ion.

2. Fabric softeners as claimed in claim 1, which contain the active ingredient of the formula I in an amount of from 1 to 15% by weight.

3. Fabric softeners as claimed in claim 1, which contain the active ingredient of the formula I in an amount of from 20 to 35% by weight.

* * * * *